United States Patent
Mogna et al.

(10) Patent No.: US 9,833,484 B2
(45) Date of Patent: Dec. 5, 2017

(54) CONJUGATED LINOLEIC ACID-PRODUCING STRAINS OF PROBIOTIC BACTERIA AND USE THEREOF FOR THE PREPARATION OF A FOOD, DIETETIC OR PHARMACEUTICAL COMPOSITION

(71) Applicants: Giovanni Mogna, Novara (IT); Gian Paolo Strozzi, Novara (IT); Marco Pane, Novara (IT)

(72) Inventors: Giovanni Mogna, Novara (IT); Gian Paolo Strozzi, Novara (IT); Marco Pane, Novara (IT)

(73) Assignee: ALCE NORTH AMERICA, INC., Arlington Heights, IL (US)

( * ) Notice: Subject to any disclaimer, the term of this patent is extended or adjusted under 35 U.S.C. 154(b) by 0 days.

(21) Appl. No.: 14/308,606

(22) Filed: Jun. 18, 2014

(65) Prior Publication Data

US 2015/0023925 A1    Jan. 22, 2015

Related U.S. Application Data

(63) Continuation of application No. 13/516,579, filed as application No. PCT/IB2010/003244 on Dec. 14, 2010, now abandoned.

(30) Foreign Application Priority Data

Dec. 16, 2009  (IT) .............. RM2009A0662
Dec. 3, 2010   (IT) .............. MI2010A2235

(51) Int. Cl.
| | | |
|---|---|---|
| A01N 63/00 | (2006.01) | |
| A61K 35/745 | (2015.01) | |
| A61K 35/74 | (2015.01) | |
| C12P 7/64 | (2006.01) | |
| C12R 1/01 | (2006.01) | |
| A61K 35/741 | (2015.01) | |
| C12N 1/20 | (2006.01) | |
| A61K 35/00 | (2006.01) | |

(52) U.S. Cl.
CPC ............ *A61K 35/745* (2013.01); *A61K 35/74* (2013.01); *A61K 35/741* (2013.01); *C12N 1/20* (2013.01); *C12P 7/6427* (2013.01); *C12R 1/01* (2013.01); *A61K 2035/115* (2013.01)

(58) Field of Classification Search
None
See application file for complete search history.

(56) References Cited

U.S. PATENT DOCUMENTS 7,223,543 B2 *  5/2007  Stanton et al. ............... 435/134

FOREIGN PATENT DOCUMENTS

| WO | WO 2006/039768 | * | 4/2006 |
| WO | WO 2009/043856 | * | 4/2009 |
| WO | WO 2010/103374 | * | 9/2010 |

OTHER PUBLICATIONS

Lammers et al. FEMS Immunology and Medical Microbiology. 2003, 38:165-172.*
Deok Kun Oh et al. "Production of conjugated linoleic acid by isolated Bifidobacterium strains". World Journal of Microbiology and Biotechnology, 2003, 19: 907-912.*

* cited by examiner

*Primary Examiner* — Vera Afremova
(74) *Attorney, Agent, or Firm* — McCarter & English, LLP; Danielle L. Herritt; Jill Ann Mello

(57) ABSTRACT

The present invention relates to conjugated linoleic acid (CLA)-producing strains of probiotic bacteria. In particular, the present invention relates to a selection of bacterial strains belonging to the genus *Bifidobacterium* which were selected for their ability to produce conjugated linoleic acid (CLA) from linoleic acid (LA). Furthermore, the present invention relates to a food, dietetic or pharmaceutical composition comprising said bacterial strains capable of increasing the quantity of CLA in situ, i.e. inside the gastrointestinal tract.

11 Claims, 5 Drawing Sheets

FIG. 2

Table 1

| TPY broth | g/l | MRS broth | g/l | LAPTg broth | g/l |
|---|---|---|---|---|---|
| Trypticase | 10.00 | Tryptone | 10.00 | Peptone | 15.00 |
| Phytone Soytone | 5.00 | Meat extract | 10.00 | Tryptone | 10.00 |
| Yeast extract | 5.00 | Yeast extract | 5.00 | Glucose | 10.00 |
| Glucose | 10.00 | Glucose | 20.00 | Yeast extract | 10.00 |
| Tween 80 | 1.00 | Tween 80 | 1.00 | Tween 80 | 1.00 |
| $K_2HPO_4$ | 2.00 | $K_2HPO_4$ | 2.00 | | |
| $MgCl_2\ 6H_2O$ | 0.50 | Sodium acetate | 5.00 | | |
| $ZnSO_4\ 7H_2O$ | 0.25 | Diammonium citrate | 2.00 | | |
| $CaCl_2$ | 0.15 | $MgSO_4\ 7H_2O$ | 0.2 | | |
| | | $MnSO_4\ H_2O$ | 0.05 | | |

Table 2

| [CLA] mg/ml | OD233 |
|---|---|
| 0,32 | >+3 |
| 0,16 | 2,733 |
| 0,08 | 2,095 |
| 0,04 | 1,084 |
| 0,02 | 0,569 |
| 0,01 | 0,328 |

Table 3

Table 4

| LA mg/ml | TPY | MRS |
|---|---|---|
| 0 | $11 \times 10^8$ cfu | $25 \times 10^8$ cfu |
| 0.5 | $10 \times 10^8$ cfu | $6 \times 10^8$ cfu |
| 1 | $9.5 \times 10^8$ cfu | $4 \times 10^8$ cfu |

FIG. 4

Table 5

| Strains used | OD 600 (16 h) | [CLA] mg/ml | % [CLA] | [CLA]/ OD |
|---|---|---|---|---|
| B. longum BL04 DSM 23233 | 0.918 | 0.465 | 92.93% | 0.51 |
| B. breve DSM 16604 | 1.278 | 0.393 | 71.38% | 0.31 |
| B. breve DSM 16596 | 1.092 | 0.348 | 69.53% | 0.32 |
| B. breve DSM 20213 | 1.413 | 0.342 | 68.31% | 0.24 |
| L. reuteri DSM 20016 | 1.003 | 0 | 0% | 0.00 |

Table 6

| TPY sterile broth | OD 233 nm | [CLA] mg/ml |
|---|---|---|
| TPY + 0 mg/ml LA | 0.987 | 0.0362 |
| TPY + 0.5 mg/ml LA | 1.003 | 0.0369 |

FIG. 5

Table 7

| Strains | Biological fluids | After different contact times (minutes)* | | In the presence of bile in the medium** |
|---|---|---|---|---|
| | | 5' | 30' | |
| Bifidobacterium longum BL04 DSM 23233 | Human gastric juice | 80 | 36 | |
| | Simulated gastric juice | 90 | 30 | |
| | Simulated pancreatic secretion | 91 | 60 | |
| | Human bile | | | 65 |
| | Bile salts | | | 62 |
| Bifidobacterium breve BR03 DSM 16604 | Human gastric juice | 92 | 34 | |
| | Simulated gastric juice | 96 | 40 | |
| | Simulated pancreatic secretion | 91 | 42 | |
| | Human bile | | | 35 |
| | Bile salts | | | 10 |
| Bifidobacterium breve BR04 DSM 16596 | Human gastric juice | 87 | 57 | |
| | Simulated gastric juice | 91 | 33 | |
| | Simulated pancreatic secretion | 89 | 77 | |
| | Human bile | | | 84 |
| | Bile salts | | | 55 |
| Bifidobacterium breve DSM 20213 | Human gastric juice | 82 | 55 | |
| | Simulated gastric juice | 84 | 31 | |
| | Simulated pancreatic secretion | 86 | 69 | |
| | Human bile | | | 67 |
| | Bile salts | | | 22 |

- (*) the table shows the percentage of survival of the bacterial strains in two different types of gastric juices and simulated pancreatic secretion at 37°C after differenti contact times (5 and 30 minutes)
- (**) the results of survival in the presence of a bile secretion were obtained by comparing the number of colonies that grew in the culture medium with and without the addition of bile salts or human bile.

CONJUGATED LINOLEIC ACID-PRODUCING STRAINS OF PROBIOTIC BACTERIA AND USE THEREOF FOR THE PREPARATION OF A FOOD, DIETETIC OR PHARMACEUTICAL COMPOSITION

RELATED APPLICATIONS

The present application is a continuation application of U.S. patent application Ser. No. 13/516,579, filed on Dec. 17, 2012; which is a U.S. national stage application filed under 35 U.S.C. §371, based on International Application No. PCT/IB2010/003244, filed on Dec. 14, 2010, which claims the benefit of priority to Italian Patent Application Nos. RM2009A000662, filed on Dec. 16, 2009, and MI2010A002235, filed on Dec. 3, 2010. The entire contents of the foregoing applications are hereby incorporated herein by reference.

The present invention relates to conjugated linoleic acid (CLA)-producing strains of probiotic bacteria. In particular, the present invention relates to a selection of bacterial strains belonging to the genus *Bifidobacterium* which were selected for their ability to produce conjugated linoleic acid (CLA) from linoleic acid (LA). Furthermore, the present invention relates to a food, dietetic or pharmaceutical composition comprising said bacterial strains and capable of increasing the quantity of CLA in situ, i.e. inside the gastrointestinal tract.

The use of conjugated linoleic acid (CLA) in the preparation of food products and supplements is known.

The development of said preparations is tied to the beneficial effects provided by CLA inside the body.

However, in the past thirty years, the dietary intake of CLA has drastically decreased for two fundamental reasons.

Firstly, the consumption of pork and milk derivatives, which represent the principal sources of these molecules, has greatly decreased.

Secondly, modern livestock rearing techniques have led pasture grass and forage to be replaced with industrially produced feedstuffs, which do not contain much natural linoleic acid.

Adding CLA to a food substrate to preparare CLA-rich/supplemented foods is known. However, said food products enriched/supplemented with CLA present a number of drawbacks and limits of application due to the fact that the oral administration thereof does not always represent a valid and effective way of delivering CLA into the body; in particular the in situ delivery of CLA in the gastrointestinal tract of interest is very compromised and limited. Moreover, in some countries the direct addition of CLA, as an active ingredient, to food products is not always allowed.

There is thus a need to have a composition which is capable of overcoming the limits of the prior art and of representing a valid, effective means of delivering CLA into the body.

The excess of linoleic acid in the modern human diet is due not only to a low consumption of fish, but also to a high consumption of products rich in vegetable oils and seeds. This situation is not, moreover, characteristic solely of the human diet, but rather also extends to the diet of animals used for food, which are commonly fed grain.

All this is reflected in a worse ratio between ω6 fatty acids and ω3 fatty acids in meat products, dairy products and eggs, which are among the foods most widely consumed in the diet.

However, an improvement in the ω6/ω3 ratio by dietary means alone today presents a number of difficulties and problems unlikely to be overcome, since said problems are tied to the production and marketing systems, which are managed on an industrial scale and thus difficult to modify.

Therefore, it becomes necessary to be able to reduce the quantity of linoleic acid (LA) deriving from the diet, which accumulates in excess in the body.

The subject matter of the present invention relates to a selection of strains of probiotic bacteria capable of converting linoleic acid (LA) into conjugated linoleic acid (CLA), as claimed in the appended claim.

The subject matter of the present invention further relates to a food or dietetic or pharmaceutical composition, as claimed in the appended claim.

The subject matter of the present invention further relates to a pharmaceutical composition for use as a medication, as claimed in the appended claim.

The subject matter of the present invention further relates to the use of at least one bacterial strain capable of converting LA into CLA for the preparation of a composition, as claimed in the appended claim.

Further preferred embodiments of the present invention will be described and illustrated below, without being in any way intended to limit the scope of the present invention.

BRIEF DESCRIPTION OF DRAWINGS

FIG. 2, Table 1 shows the qualitative and quantitative composition of three culture media used in the present invention: TPY, MRS and LATPg. FIG. 2, Table 2 shows the absorbance values obtained from the spectrophotometric reading at a wavelength of 233 nm with respect to the concentrations of CLA.

FIG. 3, Table 4 shows the pour plate counts obtained using the TPY and MRS culture media at different concentrations of LA.

FIG. 4, Table 5 shows the values obtained for the concentration of CLA/ml produced; percentage of LA-CLA conversion (expressed as CLA produced/0.50 mg/ml LA); CLA concentration ratio/OD 600 nm. FIG. 4, Table 6 shows the quantification of CLA present in the TPY culture medium with and without inoculation of LA.

FIG. 5, Table 7 shows the resistance of selected strains to gastric juices, bile and pancreatic secretion.

Figure 1:
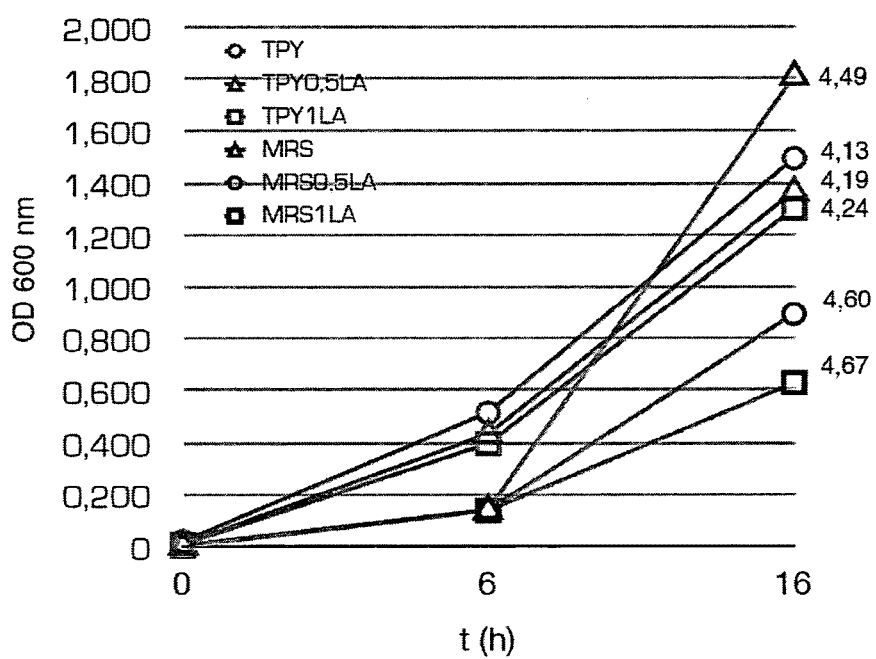
FIG. 1 shows the growth curves in time of the strain *B. breve* DSM 20213 in TPY and MRS broth at different concentrations of LA (0, 0.5 and 1 mg/ml). The initial pH for the TPY culture broth is 6.11; for MRS it is 5.83. The final pH values are given in the figure itself.
Figure 3:
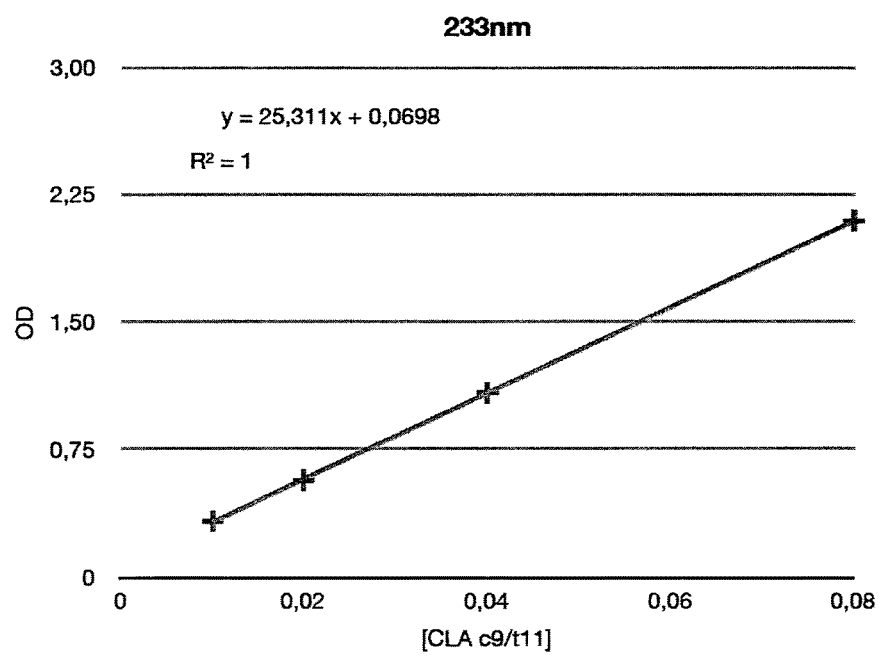
FIG. 3, Table 3 shows the regression line obtained with the values shown in table 2.

All strains have been deposited in accordance with the Treaty of Budapest and are accessible to the public on request from the competent Depositing Authority. Such Depositing Authorities include DSMZ (Deutsche Sammlung von Mikroorganismen and Zellkulturen GmbH; Inhoffenstr. 7B, D-38124 Braunschweig, Germany).

By virtue of intense research activity, the Applicant has succeeded in selecting specific strains of probiotic bacteria, belonging to the genus *Bifidobacterium*.

Advantageously, said strains belong to the species *B. longum* and *B. breve*.

In particular, the strains selected by the Applicant are selected from the group comprising:

*Bifidobacterium longum*, deposited with the DSMZ and having the accession number DSM 23233, filing date 12 Dec. 2010, depositor Probiotical S.p.A.;

*Bifidobacterium breve*, deposited with the DSMZ and having the accession number DSM 16604, filing date 20 Jul. 2004, depositor Probiotical S.p.A.;

*Bifidobacterium breve*, deposited with the DSMZ and having the accession number DSM 16596, filing date 21 Jul. 2004, depositor Probiotical S.p.A.;

*Bifidobacterium breve*, deposited with the DSMZ and having the accession number DSM 20213.

The Applicant has surprisingly found that the selected strains belonging to the genus *Bifidobacterium* are capable of converting linoleic acid (LA) into conjugated linoleic acid (CLA), with a conversion rate greater than 65%.

Advantageously, the selected strains are capable of converting linoleic acid (LA) into conjugated linoleic acid (CLA), with a conversion rate greater than 70%; even more advantageously, greater than 90%.

In the context of the present invention, LA means an omega-6 unsaturated fatty acid called [cis, cis-9,12-octadecadienoic acid] CAS N. 60-33-3 (also known as 18:2(n-6)).

In the context of the present invention, CLA means a group of at least 28 isomers of linoleic acid found, for example, in meat and in dairy products. The group comprises the isomer [cis-9,trans-11] and the isomer [trans-10, cis-12], among others.

In the context of the present invention, conversion of LA into CLA refers to the obtainment of a mixture comprising the isomer [cis-9,trans-11] and the isomer [trans-10,cis-12], where the former is present in larger quantity or, alternatively, to the obtainment solely of the isomer [cis-9,trans-11].

All of the strains tested by the Appliicant are of human origin and were isolated from faecal material.

Moreover, the selected strains were also tested to verify their resistance to gastric juices, bile and pancreatic secretion.

The results are shown in table 7.

In table 7, (*) indicates the survival of probiotic strains in two different types of gastric juices and in a simulated pancreatic secretion at 37° C. after different contact times (5 and 30 minutes).

In table 7, (**) indicates the results of survival in the presence of biliary secretion, assessed by comparing the number of colonies grown in a culture medium "with" and "without" the addition of bile salts or human bile.

From these tests it emerged that a significant percentage of ingested cells are able to overcome the gastric acidity barrier and pass beyond the intestine.

This aspect is of particular importance as it guarantees that a sufficient number of viable cells are able to reach the intestine, where the transformation of linoleic acid (LA) into its conjugated form (CLA) takes place.

Advantageously, the bacteria contained in the composition of the present invention are able to overcome the gastric barrier and duodenal transit, thus enabling colonisation of the gastrointestinal tract and the conversion of LA into CLA directly in situ, preferably in the gastrointestinal tract.

Although the mechanism of conversion from LA into CLA is not wholly clear at present, it seems that the bacterial strains adopt a detoxification strategy, transforming LA into its conjugated form CLA and removing LA from the environment in which it is present in excess.

In a preferred embodiment, the food or dietetic or pharmaceutical composition of the present invention comprises, or alternatively consists of, at least one strain belonging to the species *B. breve*, selected from the group *B. breve* DSM 16604, *B. breve* DSM 16596 and *B. breve* DSM 20213.

Advantageously, the food or dietetic or pharmaceutical composition of the present invention comprises, or alternatively consists of, *B. breve* DSM 16604.

In another preferred embodiment, the food or dietetic or pharmaceutical composition of the present invention comprises or consists of at least two strains belonging to the species *B. breve*, selected from the group *B. breve* DSM 16604, *B. breve* DSM 16596 and *B. breve* DSM 20213.

Advantageously, the food or dietetic or pharmaceutical composition of the present invention comprises, or alternatively consists of, *B. breve* DSM 16604 and *B. breve* DSM 16596.

Advantageously, the food or dietetic or pharmaceutical composition of the present invention comprises, or alternatively consists of, *B. breve* DSM 16604 and *B. breve* DSM 20213.

Advantageously, the food or dietetic or pharmaceutical composition of the present invention comprises, or alternatively consists of, *B. breve* DSM 16596 and *B. breve* DSM 20213.

In another preferred embodiment, the food or dietetic or pharmaceutical composition of the present invention comprises, or alternatively consists of, at least three strains belonging to the species *B. Breve*, selected from the group *B. breve* DSM 16604, *B. breve* DSM 16596 and *B. breve* DSM 20213.

In another preferred embodiment, the food or dietetic or pharmaceutical composition of the present invention comprises:

*Bifidobacterium breve*, deposited with the DSMZ and having the accession number DSM 16604, filing date 20 Jul. 2004, depositor Probiotical S.p.A., and/or

*Bifidobacterium breve*, deposited with the DSMZ and having the accession number DSM 16596, filing date 21 Jul. 2004, depositor Probiotical S.p.A., and/or

*Bifidobacterium breve*, deposited with the DSMZ and having the accession number DSM 20213.

If two species of *B. Breve* are used, the ratio of viable cells is comprised from 1:3 to 3:1, preferably 1:1.

If three species of *B. Breve* are used, the ratio of viable cells is comprised from 3:1:1 to 1:1:1 (*B. breve* DSM 16604: *B. breve* DSM 16596: *B. breve* DSM 20213).

In a preferred embodiment, the food or dietetic or pharmaceutical composition of the present invention comprises, or alternatively consists of, *Bifidobacterium longum* BL04, DSM 23233.

In another preferred embodiment, the food or dietetic or pharmaceutical composition of the present invention comprises, or alternatively consists of, *Bifidobacterium longum* BL04, DSM 23233, in association with at least one of the following strains: *Bifidobacterium breve* DSM 16604, *Bifidobacterium breve* DSM 16596 or *Bifidobacterium breve* DSMZ 20213.

Advantageously, the food or dietetic or pharmaceutical composition of the present invention comprises, or alternatively consists of, *Bifidobacterium longum* BL04 DSM 23233 and *Bifidobacterium breve* DSM 16604.

Advantageously, the food or dietetic or pharmaceutical composition of the present invention comprises, or alternatively consists of, *Bifidobacterium longum* BL04 DSM 23233 and *Bifidobacterium breve* DSM 16596.

Advantageously, the food or dietetic or pharmaceutical composition of the present invention comprises, or alternatively consists of, *Bifidobacterium longum* BL04 DSM 23233 and *Bifidobacterium breve* DSM 20213.

In another preferred embodiment, the food or dietetic or pharmaceutical composition of the present invention comprises, or alternatively consists of, *Bifidobacterium longum* BL04, DSM 23233, in association with at least two of the following strains: *Bifidobacterium breve* DSM 16604, *Bifidobacterium breve* DSM 16596 or *Bifidobacterium breve* DSMZ 20213.

Advantageously, the food or dietetic or pharmaceutical composition of the present invention comprises, or alternatively consists of, *Bifidobacterium longum* BL04 DSM 23233, *Bifidobacterium breve* DSM 16604 and *Bifidobacterium breve* DSM 16596.

Advantageously, the food or dietetic or pharmaceutical composition of the present invention comprises, or alternatively consists of, *Bifidobacterium longum* BL04 DSM 23233, *Bifidobacterium breve* DSM 16604 and *Bifidobacterium breve* DSM 20213.

Advantageously, the food or dietetic or pharmaceutical composition of the present invention comprises, or alternatively consists of, *Bifidobacterium longum* BL04 DSM 23233, *Bifidobacterium breve* DSM 16596 and *Bifidobacterium breve* DSM 20213.

In another preferred embodiment, the food or dietetic or pharmaceutical composition of the present invention comprises, or alternatively consists of, *Bifidobacterium longum* BL04, DSM 23233, in association with at least three of the following strains: *Bifidobacterium breve* DSM 16604, *Bifidobacterium breve* DSM 16596 and *Bifidobacterium breve* DSMZ 20213.

Advantageously, the food or dietetic or pharmaceutical composition of the present invention comprises, or alternatively consists of, *Bifidobacterium longum* BL04 DSM 23233, *Bifidobacterium breve* DSM 16604, *Bifidobacterium breve* DSM 16596 and *Bifidobacterium breve* DSM 20213.

The ratio, in terms of viable cells, between *Bifidobacterium Longum*, BL04, DSM 23233 and the above-mentioned set of strains of *Bifidocbacterium breve* is comprised from 1:3 to 3:1, preferably 1:1.

In a preferred embodiment, the pharmaceutical composition containing the bacterial strains as specified above is indicated for use as a medication, preferably as an anti-inflammatory, in particular for the preventive and/or curative treatment of intestinal disorders, diarrhea and inflammation of the colon, increasing the lean body mass, increasing thermogenesis, cancer prevention and protection against oxidative stress.

The composition of the present invention has application in the preventive or curative treatment of conjugated linoleic acid deficiencies.

The composition of the present invention can be formulated in solid, lyophilised or dried form, for example in powder or granular form.

Moreover, one pharmaceutical form of interest is tablets or hard or soft gelatin capsules.

Insofar as tablets are concerned, these may comprise an inner part comprising the bacterial strains and an outer coating part. The coating may comprise water-soluble polymers and/or polymers able to withstand the pH variations in the stomach and enable passage into the intestinal tract.

Another aspect of the invention relates to a method for the production of conjugated linoleic acid.

The method involves a step wherein one or more bacterial strains, as specified above, are cultivated/fermented in the presence of linoleic acid and the conjugated linoleic acid formed is subsequently isolated.

The method can be carried out in a laboratory or on an industrial scale.

Another aspect of the invention relates to the conversion from LA to CLA directly in the body once an individual has taken the composition of the present invention.

The conjugated linoleic acid that is obtained in larger quantity is the isomer [cis-9, trans-11 octadecadienoic acid], as compared to the isomer [trans-10, cis 12].

Another aspect of the invention relates to the use of at least one bacterial strain, as specified above, to prepare a composition for the treatment of disorders or pathologies connected to a deficiency of linoleic acid derivatives.

The Applicant conducted intense research activity on an extremely vast group of bacterial strains. All of the bacterial strains were tested and selected based on their ability/capability to convert LA into CLA.

The Applicant developed a culture medium suitable for carrying out the selection of strains and perfected the spectrophotometric techniques used to carry out the selection of CLA-producing bacterial strains, with readings at a wavelength of 233 nm.

Linoleic acid toxicity test and choice of culture medium. The strain *B. breve* DSMZ 20213 was selected as candidate for the linoleic acid toxicity test. Said strain, in fact, is able to grow in the presence of LA and displays good rates of conversion into CLA. Moreover, *B. breve* DSMZ 20213 was used for subsequent analyses as a positive control. Therefore, starting from the frozen form of said strain, it was possible to revive it in three different culture media, which are specified in table 1.

After preparation, the media were sterilized in an autoclave at 121° C. for 15'. At the end of sterilization, the pH values of the media were 6.60±0.10 at 25° C., 6.20±0.20 at 25° C. and 6.5±0.5 at 25° C., respectively, for TPY, MRS and LAPTg broth. Revival was achieved by inoculating 1% of *B. breve* DSMZ 20213 into 10 ml of the three culture media with the addition of 1% cysteine chlorohydrate (5% sol.) and subsequent incubation under anaerobic conditions using Gas-Packs at 37° C.±1° C. for 24 hours±1 hour. This operation was carried out through two successive transplants to permit complete revival of the strain.

The strain thus revived was inoculated at 1% in 10 ml of the three different culture media prepared as described above, with the addition of three solutions at different concentrations of linoleic acid, precisely 0, 0.5 mg/ml (Sigma-Aldrich cod.L1276), and then incubated in the Gas-Pack at 37±° C. for 16 hours±1 hour.

In order to simplify the operation, three LA stock solutions were produced at 0 mg/ml, 50 mg/ml and 100 mg/ml, with the addition of 2% (v/v) Tween 80 to permit the formation of an emulsion and consequent increase in the solubility of the linoleic acid dissolved using an anchor and magnetic stirrer.

Upon complete dissolution of the Tween 80, the solutions thus obtained were aliquoted and frozen at −25±1° C. following filtration with a 0.20 μm filter.

A count was carried out by means of spectrophotometric reading at 600 nm at the start, at 6 hours and at the end of the incubation period. The pH was recorded at the start and at the end of the incubation period.

Preparation of the Regression Line The regression line constructed for c9/t11 CLA concentrations of 320, 160, 80, 40, 20 and 10 μg/ml hexane demonstrated that concentrations from 10 to 80 μg/ml were associated with a linear increase in the absorbance values at 233 nm ($R^2=1$).

However, when the regression line was also calculated with the absorbance value obtained for the concentration of 160 μg/ml, the line lost its linear pattern and became polynomial, thus precluding a precise quantification of the CLA concentrations for absorbances of between 2.095 and 2.733. At concentrations equal to and greater than 320 µg/ml, the spectrophotometer gave non-quantifiable absorbance (>+3).

Therefore, the concentration of CLA present in the supernatants of the absorbance cultures<2.095 can be directly calculated with the equation y=25.311x+0.0698. For samples that gave readings above 2.095, recourse was made to the expedient of 1:2 serial dilutions.

Relying on a 1:2 serial dilution of the sample we thus brought the absorbance values back within the interval which guarantees linearity, and hence the applicability of the equation. The data are shown in Table 2.

To obviate the difficulty of assaying c9/t11 CLA (in the preparation of the first dilution necessary for calculating the regression line) due to its viscosity, and to guarantee maximum precision, we used a 2 µl fixed volume pipette with glass capillaries.

The 2 µl sample of c9/t11 CLA thus obtained was then diluted with 1.450 ml of hexane in a 2 ml test tube.

We thus obtained a starting concentration of 1280 µg/ml (density c9/t11=0.903 mg/µl). 1:2 serial dilutions were made from this concentration until arriving at a concentration of 10 µg/ml. To limit evaporation of the hexane as much as possible, the various serial dilutions were performed in 200 µl micro test tubes previously filled with 100 µl of hexane and then immediately closed. The various dilutions were then obtained serially by adding 100 µl of the previous solution, starting from the mother solution at 1280 µg/ml.

At the end of the preparation of the various dilutions, we took a spectrophotometer reading of the optical density at a wavelength of 233 nm, using quartz cuvettes with a nominal capacity of 100 µl. Said operation was carried out starting from the solution with the lowest concentration (10 µg/ml).

The absorbance values thus obtained are shown in table 3.

Fatty Acid Extraction.

After a selection had been made as to the suitable culture medium and LA concentrations to be used, they were thawed and reactivated.

The strain *B. breve* DSMZ 20213 was selected as a positive control. The same procedure was also applied on a sample of culture medium prepared without inoculum and with the addition of LA, to be used as a blank sample.

The TPY broth, after being supplemented with 1% of cysteine chlorohydrate (5% sol.), was selected as the culture medium for the steps of reactivation and growth in the presence of 0.5 mg/ml of LA.

At the end of the incubation period, the culture broth and blank sample were centrifuged at 5000 g for 5' and the supernatants were aliquoted in amounts of 500 µl in 1.5 ml test tubes per microcentrifuge.

Then followed double hexane extraction according to the method of Yung et al., 2006 (Reference 1), with the modifications described below. The extraction involved the addition of 500 µl of hexane to the aliquoted supernatants and blank sample. The samples were then mixed by inversion for 10', with care being taken not to break the interface between the two steps, and then allowed to rest for 30' at room temperature. At the end of the rest period, the samples were centrifuged at 2000 g for 5' to facilitate the operations of withdrawing the upper hexane phase. Once the upper hexane phase had been withdrawn and stored in a 2 ml test tube, the lower phase was again treated as described above with 500 µl of hexane. The upper phase was added to the previous one and mixed by tilting.

Spectrophotometric Analysis.

The CLA produced was quantified by means of a spectrophotometer reading of optical density using a wavelength of 233 nm, according to the method of Barrett et al., 2007 (Reference 2) and Xu et al., 2008 (Reference 3).

Before the analysis was conducted, the spectrophotometer was zeroed against 100 µl of hexane using a quartz cuvette.

A reading was then taken for all of the samples, starting from the blank; care was taken to rinse the cuvette with hexane before proceeding with the transfer of the sample.

For samples that gave absorbance values>+3, 1:2 serial dilutions in hexane were performed until reaching absorbance values such as to allow calculation of the CLA concentrations by interpolation of the straight line Y=25.311 x+0.0698.

Spectrophotometric techniques for the quantification of CLA produced by bacterial cultures are known from Barrette et al., 2007. This spectrophotometric technique is based on a characteristic of conjugated dienes (in this case CLA) to possess a UV spectrum typical of this class of compounds, with an absorbance of 233 nm. Said method, in any case, permits a quantification of the CLA produced.

Linoleic Acid Toxicity Test and Selection of Culture Medium.

At the end of the incubation period (16 hours±1 hour, 37±1° C.), the toxicity test conducted on the strain *B. breve* DSM 20213 using different LA concentrations (0, 0.5 and 1 mg/ml) in three different culture media (TPY, MRS and LAPTg) made it possible to identify the most suitable culture medium for carrying out the subsequent screening step. TPY broth was selected as a culture medium as it provided the environmental conditions most favourable to the growth of Bifidobacteria in the presence of LA. With TPY broth we found the least variability in counts taken both via spectrophotometer readings of optical density with a wavelength of 600 nm and counts by the pour plate method, FIG. 1 and table 4.

The differences observed in the use of TPY, MRS and LAPTg broth at different LA concentrations (0, 035, 1 mg/ml) (FIG. 1) highlighted the importance of the culture medium in studies regarding microbial metabolism.

In fact, the use of TPY broth proved to be preferable to the use of MRS and LAPTg broth, as it gave the least variability in microbial growth at different LA concentrations, as well as the highest counts, LA concentrations being equal (0.5 and 1 mg/ml), compared to MRS and LAPTg broth. The initial LA concentration selected was 0.5 mg/ml. This concentration is in fact the preferable one for the LA-to-CLA conversion tests in MRS broth conducted in other studies (Barrett et al., 2007 and Xu et al., 2008). The selection was dictated by the wish to compare, in a preliminary phase, the conversion rates obtained using TPY broth as the culture medium and those reported in the literature with regard to the use of MRS broth as the culture medium.

Selection of CLA-Producing Strains of Bifidobacteria.

At the end of the incubation period (16 hours±1 hour, 37±1° C.), the above-specified bacterial strains and the negative control *Lb. Reuteri* DSM 20016 were submitted to spectrophotometric analysis at 233 nm, the procedure necessary for quantifying the CLA produced. Table 5 shows the results obtained with respect to the conversion of LA into CLA by the different selected strains of Bifidobacteria.

The strain *B. longum* DSM 23233 showed to be the largest producer of CLA, with a production of 0.465 mg/ml, equal to an LA-to-CLA conversion rate of 92.93%. While the strain *B. breve* DSM 16604 showed to be a good producer of CLA, with a production of 0.393 mg/ml, equal to an LA-to-CLA conversion rate of 71.38%.

The CLA concentrations produced were calculated assuming that the culture media contained from the start variable quantities of LA and CLA due to the presence of ingredients such as meat extracts, yeast extract, soybean components, etc. In this regard, we compared the spectrophotometer readings of optical density at the wavelength of 233 nm for the different sterile media with and without LA at 0.5 mg/ml. The results obtained (table 6) revealed no significant difference between the sterile medium with and without the addition of 0.5 mg/ml of LA.

The foregoing results confirmed the ability of the technique used to quantify exclusively the acidic component characterised by having two conjugated double bonds, as in the case of CLA. Finally, the calculated quantity of CLA present in the sterile culture media was subsequently subtracted in the calculation of the concentrations of CLA produced by microbial activity. Furthermore, the bacterial count performed by means of spectrophotometer readings of optical density (wavelength 600 nm) showed a higher count for *L. reuteri* DSM 20016 versus the CLA-producing strains, suggesting that toxicity related to the presence of LA is strain specific.

Based on these results, it may be deduced that the most highly sensitive microorganisms are also the ones that are capable of achieving the greatest conversion of LA to CLA, probably as a mechanism of defence against the toxic element.

The tests performed as described above reveal a high percentage of conversion for *B. longum* DSM 23233 (92.93%) and *B. breve* DSM 16604 (71.38%) as compared to the positive control *B. breve* DSM 20213, relative to a study previously conducted using MRS broth (Barrett et al., 2007).

Therefore, the activity of conversion from LA to CLA performed by Bifidobacteria could make this metabolite directly available in the intestinal lumen, where it could manifest its health-promoting properties both locally and following its absorption.

The foregoing results reveal the ability of several strains of Bifidobacteria (in particular as regards the species *B. longum* and *B. breve*) to convert linoleic acid into conjugated linoleic acid. Accordingly, the use of such strains in the probiotic realm could represent an efficacious and innovative means for controlling the delicate balance in the dietary intake of omega-6/omega-3 EFAs.

The strains of Bifidobacteria capable of converting LA to CLA could interact in situ, along the gastrointestinal tract, with the essential fatty acids taken in through the diet, potentially opposing the pro-inflammatory metabolism of the pathway of omega-6 fatty acids and producing metabolites (CLA) with a possible nutraceutic role. In fact, even though the majority of the fats taken in through the diet are digested in the small intestine, approximately 5-8 g of lipids reach the colon every day. Furthermore, it has been estimated that humans expel around 20 mg of LA through faeces. This suggests that LA is potentially usable as a substrate for the production of CLA. In addition, the recent isolation of strains of Bifidobacteria and *Lactobacilli* from the small intestine of newborn babies extends the applicability of CLA-producing strains of Bifidobacteria. These findings suggest a scope of applicability extending to nearly the entirety of the gastrointestinal tract, with the possibility of an action that is potentially simultaneous with lipid absorption, which occurs mainly in the upper regions of the small intestine. Finally, the applicability of CLA-producing probiotic strains seems promising also because the anticarcinogenic effect of CLA could manifest itself at very low concentrations. In animal models, anticarcinogenic effects have been observed for quantities of CLA equivalent to 0.5-1% (w/w) of the daily diet.

LIST OF REFERENCES

1) M. Y. Young et al., *Technical Note: Improved Extraction Method with Hexane for Gas Chromatograpic Analysis of Conjugated Linoleic Acids*, J. Diary Sci. 89:90-94, American Diary Science Association, 2006.

2) E. Barrett et al., *Rapid Screening Method for Analyzing the Conjugated Linoleic Acid Production Capabilities of Bacterial Cultures*, Applied and Environmental Microbiology, April 2007, p. 2333-2337, American Society for Microbiology.

3) H. Xu et al., *Kinetics of microbial hydrogenation of free linoleic acid to conjucated linoleic acids*, Journal of Applied Microbiology, ISSN 1364-5072.

The invention claimed is:

1. A method for treating a subject suffering from a disorder or pathology connected to a deficiency in conjugated linoleic acid, the method comprising administering to said subject a composition comprising an effective amount of a bacterial strain *Bifidobacterium longum* deposited with the DSMZ on Jan. 12, 2010 under accession number DSM 23233 (*Bifidobacterium longum* DSM 23233), thereby treating said subject for a disorder or pathology connected to a deficiency in conjugated linoleic acid.

2. The method of claim 1, wherein the composition further comprises at least one bacterial strain selected from the group consisting of *Bifidobacterium breve*, deposited with the DSMZ under accession number DMS 20213 (*Bifidobacterium breve* DMS 20213), *Bifidobacterium breve*, deposited with the DSMZ on Jul. 20, 2004 under accession number DSM 16604 (*Bifidobacterium breve* DSM 16604) and *Bifidobacterium breve*, deposited with the DSMZ on Jul. 21, 2004 under accession number DSM 16596 (*Bifidobacterium breve* DSM 16596).

3. The method of claim 2, wherein the composition comprises *Bifidobacterium breve* DSM 16604.

4. The method of claim 2, wherein the composition comprises *Bifidobacterium breve* DSM 16596.

5. The method of claim 2, wherein the composition comprises *Bifidobacterium longum* DSM 23233, *Bifidobacterium breve* DSM 16604 and *Bifidobacterium breve* DSM 20213.

6. The method of claim 2, wherein the composition comprises *Bifidobacterium longum* DSM 23233, *Bifidobacterium breve* DSM 16596 and *Bifidobacterium breve* DSM 20213.

7. The method of claim 2, wherein the composition comprises *Bifidobacterium longum* DSM 23233, *Bifidobacterium breve* DSM 16604, *Bifidobacterium breve* DSM 16596 and *Bifidobacterium breve* DMS 20213.

8. The method of claim 2, wherein ratio of a number of viable cells of *Bifidobacterium longum* DSM 23233 to the number of viable cells of all *Bifidobacterium breve* strains is between 1:3 and 3:1 in the composition.

9. The method of claim 8, wherein the ratio is 1:1.

10. A method for treating a subject suffering from inflammation, the method comprising administering to said subject a composition comprising an effective amount of a bacterial strain *Bifidobacterium longum* DSM 23233, thereby treating said subject for inflammation.

11. The method of claim 10, wherein the composition further comprises at least one bacterial strain selected from the group consisting of *Bifidobacterium breve* DMS 20213, *Bifidobacterium breve* DSM 16604 and *Bifidobacterium breve* DSM 16596.

* * * * *